United States Patent [19]

Ethier

[11] Patent Number: 4,696,854

[45] Date of Patent: Sep. 29, 1987

[54] BILAYER SUBSTRATE

[75] Inventor: Dolores O. Ethier, White Bear Lake, Minn.

[73] Assignee: Lectec Corporation, Minnetonka, Minn.

[21] Appl. No.: 915,511

[22] Filed: Oct. 6, 1986

[51] Int. Cl.$^4$ ............................................. B32B 27/34
[52] U.S. Cl. ..................................... 428/287; 427/35; 428/284; 428/343; 428/354; 428/447; 428/451
[58] Field of Search ............... 428/266, 287, 290, 289, 428/284, 447, 451, 343, 354; 427/35

[56] References Cited

U.S. PATENT DOCUMENTS 3,485,661 12/1969 Campbell et al. .................. 428/266
4,331,727 5/1982 Maas .................................. 428/266

Primary Examiner—James J. Bell
Attorney, Agent, or Firm—James V. Harmon

[57] ABSTRACT

Porous bilayer non-woven substrates with an organic polymer on one side and a cured silicone resin on the other side. When the substrate is coated on the organic polymer side with a hydrophilic natural or synthetic pressure sensitive adhesive, a tape is produced that can be wound upon itself.

7 Claims, No Drawings

BILAYER SUBSTRATE

This invention relates to a porous non-woven bilayer substrate which is substantially similar in air porosity to an uncoated porous non-woven substrate but acts as a bilayer in structure and function. One side of the new bilayer substrate is an organic polymer matrix and the other side is a silicone resin. Substrates of the present invention are especially useful as a backing for porous pressure sensitive adhesive tapes suited for medical applications.

BACKGROUND OF THE INVENTION

This invention relates to a bilayer non-woven porous substrate in which the dominant layer is composed of organic fibers and a thinner layer thereon composed of a cured silicone resin. While acrylated silicone resin is greatly preferred, other silicone resins having release properties can be employed in the present invention in place of acrylated silicone resins. When a pressure sensitive adhesive is applied to the organic fiber surface, a pressure sensitive tape results that can be wound upon itself. In the prior art, pressure sensitive tapes of this type have required liners to be placed between the pressure sensitive surface and the front face of the tape notwithstanding the availability of a variety of low adhesion backsizes.

Silicone resins have been conventionally applied as an organic solution or water based dispersion. However, porous non-woven materials when treated in this manner do not produce a substrate of the type provided by this invention. Instead, the fibers of the organic polymer are covered at least partially with the silicone resin throughout which is undesirable, i.e., the coating soaks into the porous backing material. The present invention overcomes this problem.

Coatings often drastically reduce the porosity of fibrous substrates. Maintaining porosity at a high level is very important especially in the case of medical adhesive tapes, e.g., to prevent moisture from being trapped beneath the tape. The porous nature of the bilayer provided by the present invention is substantially the equivalent to the porosity of a fibrous organic polymer matrix prior to the application of a coating thereon.

DETAILED DESCRIPTION

The preferred organic polymer non-woven substrates are made from polyester fibers. Other fibers that could be used are polypropylene, rayon, nylon or cellulosic materials. This fibrous substrate serves as a backing for a silicone resin layer which is applied in an uncured state on one surface and then cured preferably by irradiation.

Electron beam irradiation for curing various substances is known. For example, the use of electron beam irradiation to cure pressure sensitive adhesives on a film is well known. An early teaching of such a use with pressure-sensitive adhesive tapes is taught in Hendricks, U.S. Pat. No. 2,956,904 issued Oct. 18, 1960.

Uncured acrylated resins of 100% solids and 100% reactive constituents are preferably applied to the porous organic fibrous layer with a Gravure-type press. Coating of the uncured acrylated silicone resin in liquid form can also be done by extrusion or roll presses. The amount of silicone resin applied may vary but will generally be in the range of 0.40 to 2.0 pounds per three thousand square feet.

Blends of silicone and other resins are possible. If desired, the silicone resin coating can be modified by blending the liquid silicone resin with urethane, epoxy, polyester or polyether resins.

The curing of the silicone substrate can be effectively performed by electron beam irradiation in the range of 2-3 megarads at a feed rate of 300-1500 ft./min. It is preferable to irradiate under a nitrogen atmosphere to achieve maximum results. Under these conditions, little or no residual monomers are present and the porosity of the bilayer substrate is substantially the same as that of organic polymer substrate prior to being coated.

A wide variety of pressure sensitive adhesives may be applied to the bilayer substrate of this invention on the opposite side of the organic fibrous polymeric matrix from the silicone coating to produce adhesive tapes capable of being wound upon themselves and therefore not requiring a liner. Illustrative pressure sensitive adhesives are taught in U.S. Pat. Nos. 2,341,533; 2,838,421; 2,855,925; 3,028,351; 3,249,572; 3,556,835; 3,575,911. Polyacrylic acid adhesives are known to be especially useful for painless, peeling bandage adhesives for use in medical tapes.

The invention will be better understood by reference to the following examples:

EXAMPLE I

The preferred bilayer substrate and pressure sensitive adhesive tape of this invention was made as follows:
A. In situ lamination.

A polyester based non-woven substrate produced by the Dexter Corp. of Windsor Lock, Conn. as DEX-TAPE (trademark) N7601 having the following characteristics:

| | |
|---|---|
| Basis weight (g/m$^2$) | 39 |
| Porosity 1/minute | 700 |
| Tensile (average) g/25 mm | 3150 |
| Thickness (microns) | 130 | was roll coated with a 100% solids acrylated silicone resin and immediately subjected to an electron beam source so as to form a silicone substrate on the polyester substrate, hereinafter referred to as the "bilayer substrate." The bilayer substrate was tested as follows:
A. Tape Release.

3M brand tape number 810 was adhered to both sides of the bilayer substrate. The removal force from the polyester surface was moderate, whereas the removal force from the silicone layer was low.

Similar results were obtained with other pressure sensitive adhesive tapes.
B. Hold Out Properties.

A blue dye was applied to both sides of the bilayer substrate. The exposed polyester surface was fully absorbent and penetration was complete. The silicone layer caused the dye to form beads and there was practically no penetration.
C. Porosity Tests.

Porosity measurements using a Model 4190 Gurley-Hill S-PS Densometer were taken on the polyester alone and the bilayer. The results in seconds per 300 cc were as follows:

| | 1 ply | 2 ply | 4 ply |
|---|---|---|---|
| Polyester alone | .297 | .388 | .597 |

-continued

|  | 1 ply | 2 ply | 4 ply |
| --- | --- | --- | --- |
| Bilayer (invention) | .248 | .282 | .369 |

Other tests showed that the porosity as measured is substantially the same when measured from either side of the bilayer.

Three pressure sensitive adhesive tapes from the bilayer substrate of Example I were prepared as follows:

EXAMPLE II

Tape A — Rohm and Haas, Philadelphia, Pa. acrylic based adhesive QR667.

Tape B — H. B. Fuller, St. Paul, Minn., synthetic elastomeric based adhesive Fuller 1063-Z.

Tape C — Karaya gum.

ADHESION TESTING

Tapes A and B where mated, i.e., the adhesive surface is adhered to itself, and then pulled apart. In both instances, the adhesive anchorage was comparable to the adhesion of a control tape prepared from the polyester material and identical pressure sensitive adhesives. However, in the case of the polyester material, it was necessary to apply the adhesive from a transfer tape.

These results indicate that the polyester material in the bilayer substrate functions in the same manner as the polyester alone and that the silicone layer does not have any adverse effects on the pressure sensitive adhesive tape characteristics such as is the case when silicone penetrates the non-silicone layer when the silicone is applied in a solvent or aqueous base.

TAPE AGING TESTS

Aging tests on Tapes B and C which were wound on themselves without a liner were run as follows:

A. Dry Heat.

Tapes B and C were heated in a dry oven at 50 degrees C. and observed at the end of weeks one, two, three and four. In all cases, unwind, tackiness, roll condition and wear test on the skin were rated as satisfactory except in the case of Tape C where a slight loss in tackiness was observed after three weeks.

B. Humidity Chamber

Tapes B and C were placed in a humidified chamber at 40 degrees C. and observed at the end of one, two, three and four week intervals. The roll unwinding, tackiness, roll condition and wearing on the skin were all observed to be satisfactory.

These examples demonstrate that the bilayer substrate produces results which cannot be achieved by conventional coating procedures. The invention is not, however, limited to the described coating method. Vapor deposition or U.V. curing or other processing techniques not available at this time may produce a bilayer substrate of the type that would be useful in this invention. In essence, the bilayer substrates of this invention are substantially equivalent in porosity to the organic porous substrate prior to the application of the cured silicone resin matrix.

No known technique is capable of first forming the silicone substrate by itself and then bonding it to another porous substrate. Furthermore, a thin porous layer of silicone resin would probably not have the integral strength required to process it for affixing to the organic layer.

Previously in the coating of non-woven materials, it is self-evident that normally the entire non-woven matrix would be coated to some degree. By contrast, in accordance with the present invention, a bilayer is obtained in which one side has the full characteristics of the organic fibrous matrix and the other side has the full characteristics of a silicone layer.

Many variations within the scope of the appended claims will be apparent to those skilled in the art once the principles described herein are understood.

What is claimed is:

1. An integral bilayer porous non-woven substrate in which one side comprises a fibrous organic polymeric matrix having substantially unaltered surface adhesion characteristics and the second side comprises a cured silicone resin in which said bilayer structure has substantially the equivalent air permeability of the porous substrate alone and the cured silicone layer on said second side exhibits release properties but has substantially no adverse effect upon the adhesion characteristics of said one side, said substrate being formed by (a) the application of said silicone resin in an uncured state to said second side in the absence of significant polar or nonpolar solvent whereby the uncured resin will remain at least temporarily in the vicinity of the second side of the substrate and (b) curing the uncured resin by exposure to a beam of radiation prior to saturation of the matrix by the resin.

2. The substrate of claim 1 in which the organic polymeric matrix is a polyester resin fiber sheet.

3. The substrate of claim 1 in which the organic polymeric matrix is coated with a pressure sensitive adhesive to produce a pressure sensitive tape capable of being wound upon itself.

4. The bilayer of claim 1 wherein the silicone resin is an in situ coating comprising a cured acrylated silicone resin.

5. The bilayer of claim 4 wherein the in situ coating of cured acrylated silicone has a basis weight of between about 0.40 and 2.0 pounds per three thousand square feet.

6. The combination of claim 4 wherein the bilayer is coated with pressure sensitive adhesive on a surface thereof opposite the cured silicone resin and is wound in a roll.

7. The composition of claim 1 wherein the porous non-woven substrate is a blend of fibers of at least two organic polymers.

* * * * *